US007409849B2

(12) United States Patent
Butler et al.

(10) Patent No.: US 7,409,849 B2
(45) Date of Patent: Aug. 12, 2008

(54) OIL FILTRATION SYSTEM FOR PLURAL PHASE POWER EQUIPMENT TANKS

(75) Inventors: David McMahon Butler, Lenoir City, TN (US); Johnny James Clark, Lenoir City, TN (US)

(73) Assignee: FILMAX, Inc., Loudon, TN (US)

( * ) Notice: Subject to any disclaimer, the term of this patent is extended or adjusted under 35 U.S.C. 154(b) by 433 days.

(21) Appl. No.: 10/994,658

(22) Filed: Nov. 22, 2004

(65) Prior Publication Data

US 2005/0109076 A1 May 26, 2005

Related U.S. Application Data

(60) Provisional application No. 60/524,364, filed on Nov. 22, 2003.

(51) Int. Cl.
*G01N 33/26* (2006.01)
*G01N 33/20* (2006.01)

(52) U.S. Cl. ....................... 73/19.11; 73/61.43; 336/57; 336/60; 417/426

(58) Field of Classification Search .................. 336/57; 417/286
See application file for complete search history.

(56) References Cited

U.S. PATENT DOCUMENTS

| | | | | | |
|---|---|---|---|---|---|
| 2,340,898 | A | | 2/1944 | Race | |
| 3,087,431 | A | | 4/1963 | Bagwell | |
| 3,371,299 | A | | 2/1968 | Radkowski et al. | |
| 3,844,160 | A | * | 10/1974 | Yamaoka | 73/19.11 |
| 3,894,171 | A | * | 7/1975 | Kusay | 174/14 R |
| 4,232,551 | A | | 11/1980 | Pierce | |
| 4,337,820 | A | | 7/1982 | Pierce | |
| 4,424,502 | A | | 1/1984 | Kullinger et al. | |
| 4,437,082 | A | * | 3/1984 | Walsh et al. | 336/58 |
| 4,787,822 | A | * | 11/1988 | Bennett | 417/2 |
| 5,360,033 | A | | 11/1994 | Williams et al. | |
| 5,574,214 | A | | 11/1996 | Balton et al. | |
| 5,656,999 | A | | 8/1997 | Campbell | |
| 5,691,706 | A | * | 11/1997 | Butler et al. | 340/646 |
| 5,766,464 | A | | 6/1998 | Campbell | |
| 6,052,060 | A | * | 4/2000 | Butler et al. | 340/644 |
| 6,142,744 | A | * | 11/2000 | Taylor | 417/53 |
| 6,476,723 | B1 | * | 11/2002 | Campbell et al. | 340/605 |
| 6,609,411 | B1 | | 8/2003 | Taylor et al. | |
| 2003/0039550 | A1 | * | 2/2003 | Wichert | 417/53 |

* cited by examiner

*Primary Examiner*—Devon Kramer
*Assistant Examiner*—Patrick Hamo
(74) *Attorney, Agent, or Firm*—W. Allen Marcontell

(57) ABSTRACT

Insulating oil in electric power generation, transmission and distribution equipment such as circuit breakers, regulators, phase shifters, tank diverter switches and capacitor banks for respectively separated phases of a plural phase transmission or distribution line is filtered for removal of accumulated water, carbon particles and other contaminants by filters in oil circuits respective to each phase in the plurality. Each oil circuit respective to each circuit breaker includes a respective filter and circulation pump. However, all pumps in the plural phase power system, for example, are driven by the same motor and drive line whereby a fluid condition or circulation interruption of one oil circuit that requires termination of pump operation in the one oil circuit terminates the pump operation in all oil circuits. Pump motor power is preferably drawn from an energy source that may be independent of that served by the transmission and/or distribution power source.

5 Claims, 1 Drawing Sheet

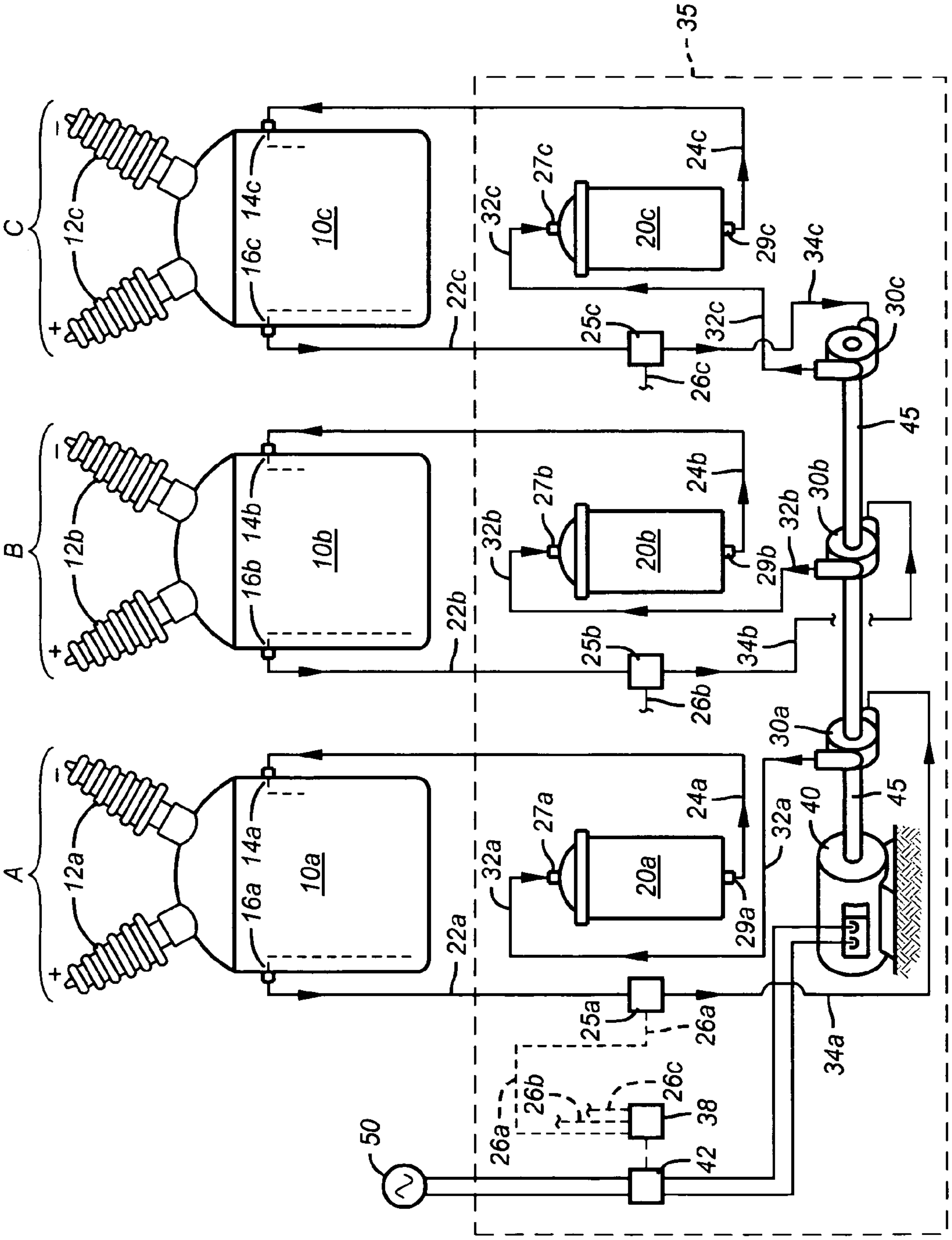
35
A
B
C
12a
12b
12c
10a
10b
10c
14a
14b
14c
16a
16b
16c
20a
20b
20c
22a
22b
22c
24a
24b
24c
25a
25b
25c
26a
26b
26c
27a
27b
27c
29a
29b
29c
30a
30b
30c
32a
32b
32c
34a
34b
34c
38
40
42
45
50

OIL FILTRATION SYSTEM FOR PLURAL PHASE POWER EQUIPMENT TANKS

CROSS-REFERENCE TO RELATED APPLICATIONS

This application claims the benefit of U.S. Provisional Application No. 60/524,364 filed Nov. 22, 2003.

STATEMENT REGARDING FEDERALLY SPONSORED RESEARCH OR DEVELOPMENT

Not Applicable

BACKGROUND OF THE INVENTION

1. Field of the Invention

The present invention relates generally to electric power transmission and distribution devices. More particularly, the invention relates to apparatus and methods for protecting a dielectric oil insulating medium used with phase switching equipment, circuit breakers, regulators, phase shifters, tank diverter switches, similar switchgear and capacitor banks for generating, transmitting and/or distributing plural phase electric power.

2. Description of Related Art

Electrical power load control and switching regulation devices for plural phase electric power generation, transmission and distribution devices such as circuit breakers, load regulators, phase shifters, tank diverter switches and similar switch gear, are often immersed in a specially compounded oil having dielectric properties for purposes of insulation, arc isolation and cooling. On occasion, these devices generate extremely high operating temperatures. Although the oil will not burn in the absence of atmosphere or oxygen, small portions will directly decompose under the intense heat of electrical arcing. This is especially true for circuit breakers, regulators and similar switchgear wherein mechanical contact switches are routinely closed and opened with a high potential difference standing at the switch contacts. As mechanical switch contact is closed or opened, brief arcing occurs. Such arcing transforms the oil by decomposition into elemental carbon which remains in the oil as suspended particles of graphite. An accumulation of suspended graphite particles will often reduce the dielectric value and hence, the insulating capacity of the oil.

Under other service circumstances and mechanisms, a dielectric oil system may also accumulate dissolved and entrained water. Water, particulate carbon and other accumulated contaminates in an oil system reduce the dielectric value of the oil and, hence, the effectiveness of the dielectric fluid to protect the internal components of the electrical apparatus.

Fortunately, contaminates such as water and carbon particles may be effectively removed from a system by filtration. Such filtration often takes the form of an external fluid circulation loop that includes a pump, a motor and a canister filter. Conduits channel a circulating flow stream of the dielectric oil between an equipment reservoir in which the electrical equipment is immersed and the filter/pumping equipment. This circulation may be continuous or intermittent.

For plural, two or three phase transmission or distribution of electrical power, each phase is carried on a separate line conduit. Regulating the power, therefore, includes individual capacitors, circuit breakers or regulators respective to each phase of the transmission. Each of these capacitors, circuit breakers or regulators may be physically positioned within a tank that confines an immersion quantity of dielectric fluid. In restatement, there is an insulating oil tank for each phase of the system. A three phase power system, therefore, has three tanks to hold three respective insulating oil reservoirs that immerse three respective switchgear devices.

A respective fluid circulation loop is preferably provided for each tank to maintain the fluid in that tank, exclusively. Hence, for the three switchgear tanks in a three phase power system, there are three respective fluid circulation loops. Each circulation loop includes a separate filter and pump respective to that circulation loop. This separation of fluids is essential to continuing load and equipment analyses of each phase since the accumulation rate and type of contaminates respective to the fluid of each phase is instructive of service needs.

When it is necessary to terminate a fluid circulation loop for one insulating oil tank respective to one power phase, whether automatically or manually, a typical operating procedure may terminate insulating oil circulation about the loops of all tanks. Although termination of all circulation loops in the event of maintenance or repair to one circulation loop is preferable, the procedure is not an absolute necessity. Normally, the circulation pumps respective to each tank in a circulation loop are driven by respective motors and connecting drive lines. Consequently, it is possible to terminate each circulation loop, selectively and individually. However, finding the volumetric space for three pumps and three motors within the permissible confines of a control cabinet becomes a challenge.

It is one objective of the present invention, therefore, to provide a system of separate circulation loops for the insulating oil in each switchgear immersion tank respective to a plural phase electrical power system wherein the circulation of insulating oil in each of the two or more circulation loops is impelled by a respective pump but that all pumps of the several circulation loops are driven by a common drive line that is controlled by a common power source.

Also an objective of the present invention is a unit of three separate pumps respective to each of three dielectric fluid circulation loops wherein all three pumps are driven by the same motor and drive line.

BRIEF SUMMARY OF THE INVENTION

The foregoing objects of the invention and others to become apparent from the detailed description of the invention to follow, may be achieved by the invention which comprises a separate insulation oil reservoir (tank) for each power control device respective to each phase of a plural (three, for example) phase power transmission or distribution system. A power control device in the context of this invention may be a circuit breaker, a voltage regulator, a phase shifter, a tank diverter switch, a phase shift capacitor or any other type of switchgear device that is operatively immersed in a dielectric fluid such as insulating oil. The dielectric fluid respective to each reservoir or tank is circulated externally of the tank through a filter and returned to the tank in a closed circulation loop. Fluid flow through each closed and independent loop is impelled by a pump respective to each circulation loop. All loop circulation pumps, however, are driven by a common power source and/or drive line whereby the termination of fluid circulation in one loop by terminating the operation of the respective pump that impels the fluid in that loop necessarily terminates the operation of all the other loop circulation pumps in the plural phase power transmission or distribution system.

Multiple properties of the dielectric fluid circulating in each circulation loop are monitored. Should the value or some predetermined combination of values arise in the fluid properties respective to one or more of the circulating fluid loops exceed predetermined limits of tolerance, system termination signals are transmitted to the common power source and/or drive line to terminate fluid circulation in all of the fluid loops.

Substantially all of the plural phase related filtration equipment including the filtration canisters, the several dielectric fluid pumps, the inter-connecting conduits, the fluid flow monitoring system and the single motor or power source frequently are operatively secured within a single, self-contained enclosure. Preferably, all of the pumps respective to plural phase oil circulation system are integrated on a common support frame or within a single housing or by the integral assembly of separate pump impeller housings whereby all of the pump impellers are driven by the same power source.

Monitors respective to fluid properties and flow parameters such as dielectric value, water content, fluid pressure, fluid flow rate and turbidity, for example, respective to each circulation loop, transmit fluid data to respective loop flow controllers. The loop flow controllers are programmed to terminate the pump operation respective to each of said circulation loops under predetermined set-points or limits of fluid pressure, fluid flow, etc. by interrupting the power supply to the single pump motor. When one loop flow controller interrupts power to the motor, the operation of all pumps in the set is therefore terminated.

BRIEF DESCRIPTION OF THE DRAWING

The invention is hereafter described in detail and with reference to the single FIGURE of the drawing wherein like reference characters designate like or similar elements throughout the FIGURE. Respective to the drawing, the invention is represented by a circulation schematic for filtered dielectric oil in a set of transmission circuit breakers for a three phase power transmission line.

DETAILED DESCRIPTION OF THE INVENTION

Referring to the drawing, three, insulating/cooling tanks 10$_a$, 10$_b$, and 10$_c$ are shown schematically to include respective pairs of external line connectors 12$_a$, 12$_b$ and 12$_c$. Electrical conduction lines respective to each of three power phases, A, B and C of an electric power transmission or distribution line are connected across each pair of connectors 12. Line continuity between the +(in) and −(out) terminals of a connector pair 12 is linked by a single phase power control and/or regulation device 10$_a$, 10$_b$, and 10$_c$ such as a circuit breaker, a voltage regulator, a tank diverter switch, a phase shifter or variable capacitor. The said single phase power control and/or regulation device 10$_a$, 10$_b$, and 10$_c$ is usually positioned internally of a respective tank. Normally, the control and/or regulation device 10$_a$, 10$_b$, and 10$_c$ is immersed in a pool of dielectric oil that is confined within the respective tank. The purpose of the oil is to cool the active, current transfer elements and suppress arcing between switch contact points upon opening and closing.

To maintain the purity of the dielectric oil within each of the tanks respective to each of the control and/or regulation devices 10$_a$, 10$_b$, and 10$_c$, respective oil filter circulation systems are provided to intermittently or continuously clean the dielectric oil of accumulated contaminants. Each of the independent filter circulation systems, respectively, comprise a canister filter 20$_a$, 20$_b$ and 20$_c$ and a pump 30$_a$, 30$_b$ and 30$_c$. The pump 30$_a$ discharge conduit 32$_a$ is connected to the inlet port 27$_a$ of respective filter canister 20$_a$. Conduit 24$_a$ connects the filter canister 20$_a$ discharge port 29$_a$ to the tank 10$_a$ inlet 14$_a$. The tank 10$_a$ outlet port 16$_a$ is shown to be connected by conduit 22$_a$ to a fluid monitor unit 25$_a$. Fluid flow from the monitor unit 25$_a$ is channeled by conduit 34$_a$ back to the suction port of the pump 30$_a$.

The dashed line boundary 35 represents equipment cabinetry that houses the filters 20$_a$, 20$_b$ and 20$_c$ the pumps 30$_a$, 30$_b$ and 30$_c$ and the motor 40. Preferably, such equipment cabinetry 35 is in the immediate proximity of the control and/or regulation devices 10$_a$, 10$_b$, and 10$_c$. In many instances, however, physical space for such cabinetry in the control or regulation device 10 is limited.

Those of skill in the art will understand the fluid monitor units 25$_a$, 25$_b$ and 25$_c$ are schematic representations of numerous instruments and sensors that measure or evaluate various properties of the fluid circulated about the respective systems. A control system such as that described by U.S. Pat. No. 6,052,060, the disclosure of which is incorporated herein by reference, is one example. Typically, the instruments may comprise pressure gages, flow rate meters, moisture ($H_2O$) meters, turbidity sensors and capacitance sensors. Other fluid properties such as pH may also be measured. It will also be understood that the instruments and sensors of the monitoring units 25$_a$, 25$_b$ and 25$_c$ may not be concentrated in one segment of the fluid circulation loop as illustrated by the drawing. Data generated by the instruments and sensors of the monitoring units 25$_a$, 25$_b$ and 25$_c$ is reported by digital or analog signals 26$_a$, 26$_b$ and 26$_c$ to a central processing unit 38. A programmed evaluation of the reported data controls the motor switch 42 and hence, operation of the motor 40. Distinctively, all three pumps 30$_a$, 30$_b$ and 30$_c$ are driven by a common motor 40 and drive line 45. Preferably, the motor 40 is energized by a power source 50 that preferably is substantially independent of the primary line power transmitted through the control and/or regulation devices 10$_a$, 10$_b$, and 10$_c$. Hence, when any of the monitors 25$_a$, 25$_b$ or 25$_c$ directs a control command to terminate fluid circulation in its respective circulation loop by interrupting the power supply to the motor 40, fluid circulation around all other loops in the system is also terminated. However, because each of the fluid loops is independent, it is possible to analyze each fluid monitor data independently for determination of the source of a problem or abnormality.

Although the several A-C phases, usually three, in a plural phase generation are generated simultaneously by the same generation source, the current and voltage of each phase of the power generation is carried on separate conduction lines A, B, and C. Correspondingly, each phase may serve separate load sources thereby requiring separate control and/or regulation. Hence, each of the phases in the generated power plurality imposes distinctive loads and loading cycles on the respective control and/or regulation devices 10$_a$, 10$_b$, and 10$_c$ and on the respective dielectric fluid systems that protect the devices. While it may be possible to physically position and operate all current, voltage and phase control devices within a plural phase power system in the same dielectric fluid pool, it would be difficult to determine which control and/or regulation device 10$_a$, 10$_b$, and 10$_c$ in a related plural phase set that was protected by a common dielectric fluid pool was the source of unusual fluid contamination. For this reason, each control and/or regulation device is preferably served by a separate and independent fluid circulation loop that is independently monitored for critical fluid properties such as pressure, flow rate, dielectric value, moisture content and/or turbidity. Should any one of the several monitors 25$_a$, 25$_b$ or 25$_c$ of the present invention detect a fluid condition in its respective circulation loop that requires the fluid circulation in that loop to be interrupted, preferably all circulation loops in the system may be interrupted at substantially the same time.

As illustrated, the common drive line 45 between the motor 40 and pumps $\mathbf{30}_a$, $\mathbf{30}_b$ and $\mathbf{30}_c$ may be a single, integral drive shaft. Those of skill in the art will recognize that the spirit of the invention may also be accomplished by other mechanical or electro-mechanical systems. Depending on the configuration of space available in the totally enclosed self-contained cabinet 35, the common drive line 45 may take other configurations such as a jackshaft drive, not illustrated, that is common to all pumps.

For example, each pump $\mathbf{30}_a$, $\mathbf{30}_b$ and $\mathbf{30}_c$ may be driven by a respective belt or chain coursed around a respective sheave or sprocket. The sprockets are mounted on a jackshaft that is relatively driven by a single motor. However, the torque transfer linkage between the jackshaft and the drive element of a respective sheave or sprocket is selectively connected by a clutch. Engagement of the clutch between the jackshaft and sheave or sprocket drive elements may be manually or electrically operated.

Although objectives similar to those of the invention may be accomplished by providing a separate motor for each pump and a common power control switch for all, the addition of two motors, associated drive linkages and controls often exceeds the cabinet volume reasonably available to the system. Hence, greater volumetric efficiency is achieved by driving all pumps with the same motor 40 and common drive line 45.

The foregoing description of the preferred embodiments of our invention have been presented for purposes of illustration and description. These embodiments are not intended to be exhaustive or to limit the invention to the precise forms disclosed. Obvious modifications or other variations are possible in light of the above teachings. The embodiments were chosen and described to provide the best illustration of the principles of the invention and its practical application and to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

We claim:

1. A method of protecting a cooperative set of power control and/or regulation devices, each device having operative control over a single power phase respective to a plural phase electric power generation, transmission or distribution line, each said device being substantially immersed in a respective reservoir of dielectric insulating fluid, said method comprising the steps of:

a. providing a separate fluid circulation loop for the insulating fluid in each reservoir, each circulation loop having a respective pump, filter and connecting fluid flow conduits;

b. providing a common drive line driven by a common power source for driving all pumps in said cooperative set;

c. providing independent fluid condition monitors for each fluid circulation loop; and, d. providing for operational termination of said common power source upon the signal command of any one of said fluid condition monitors.

2. A method of protecting a cooperative set of power control and/or regulation devices as described by claim 1 wherein each of said independent fluid circulation loops is monitored for dielectric value.

3. A method of protecting a cooperative set of power control and/or regulation devices as described by claim 1 wherein housings respective to all of said pumps are combined as an integral unit.

4. A method of protecting a cooperative set of power control and/or regulation devices as described by claim 1 further comprising a plurality of fluid condition monitors respective to each fluid circulation loop in said set.

5. A method of protecting a cooperative set of power control and/or regulation devices as described by claim 4 wherein the operation of all pumps in said set is subject to termination on the command of any one fluid condition monitor respective to any one fluid circulation loop in said cooperative set.

* * * * *